United States Patent
Sugiyama et al.

(10) Patent No.: US 9,029,333 B2
(45) Date of Patent: May 12, 2015

(54) SOLID PREPARATION FOR DIALYSIS

(75) Inventors: Yoshihiro Sugiyama, Shizuoka (JP); Yuichi Iwai, Shizuoka (JP); Michito Sumikawa, Shizuoka (JP); Naotaka Kuroda, Shizuoka (JP)

(73) Assignee: Advanced Renal Technologies, Inc., Bellevue, WA (US)

( * ) Notice: Subject to any disclaimer, the term of this patent is extended or adjusted under 35 U.S.C. 154(b) by 0 days.

(21) Appl. No.: 12/625,396

(22) Filed: Nov. 24, 2009

(65) Prior Publication Data

US 2010/0120702 A1 May 13, 2010

Related U.S. Application Data

(63) Continuation of application No. PCT/JP2008/059979, filed on May 30, 2008.

(30) Foreign Application Priority Data

May 31, 2007 (JP) ................................ 2007-145676

(51) Int. Cl.
*A61K 31/7004* (2006.01)
*A61P 13/12* (2006.01)
*A61K 31/194* (2006.01)
*A61K 33/14* (2006.01)

(52) U.S. Cl.
CPC ........... *A61K 31/194* (2013.01); *A61K 31/7004* (2013.01); *A61K 33/14* (2013.01)

(58) Field of Classification Search
None
See application file for complete search history.

(56) References Cited

U.S. PATENT DOCUMENTS 6,489,301 B1 * 12/2002 Kobira et al. ................... 514/23

FOREIGN PATENT DOCUMENTS

| EP | 1 059 083 A2 | 12/2000 |
|---|---|---|
| EP | 1 192 961 A2 | 4/2002 |
| EP | 1 731 183 A1 | 12/2006 |
| JP | 10-87478 | 4/1998 |
| JP | 2001-54570 | 2/2001 |
| JP | 2001-327597 | 11/2001 |
| JP | 2002-102337 | 4/2002 |
| JP | 2003-703 | 1/2003 |
| JP | 2005-206572 | 8/2005 |
| JP | 2005-330241 | 12/2005 |
| JP | 2006-223657 | 8/2006 |
| JP | 2007-37601 | 2/2007 |
| WO | WO 2005/094918 A1 | 10/2005 |

OTHER PUBLICATIONS

Heimlich et al. Journal of the American Pharmaceutical Association, vol. 49, No. 9, Sep. 1960.*
Clark, The Effect of Surface Area on Reaction Rates, http://www.chemguide.co.uk/physical/basicrates/surfacearea.html, 2002.*
European Office Action dated Mar. 7, 2013.

* cited by examiner

*Primary Examiner* — Layla Bland
(74) *Attorney, Agent, or Firm* — Oblon, McClelland, Maier & Neustadt, L.L.P.

(57) ABSTRACT

The present invention provides a glucose decomposition-suppressed solid preparation for dialysis among powdery or granular preparations for dialysis containing acetate-free solid organic acids as pH adjusting agents. The present invention provides the solid preparation for dialysis containing electrolytes, glucose and pH adjusting agents characterized in that solid organic acids containing reduced amount of microparticles are used, and more specifically, characterized in that solid organic acids whose 20 or less percent of particles are 250 µm or less in diameter, or solid organic acids whose 10 or less percent of particles are 150 µm or less in diameter, are used. Preferably, the solid organic acid contained therein is citric acid.

12 Claims, 2 Drawing Sheets

SOLID PREPARATION FOR DIALYSIS

CROSS REFERENCES TO RELATED APPLICATIONS

This application is a Continuation of International Patent Application No. PCT/JP08/59979, filed on May 30, 2008, and claims priority to Japanese Patent Application No. 2007-145676, filed on May 31, 2007.

TECHNICAL FIELD

The present invention relates to solid preparations for dialysis, and more specifically, to a solid preparation for dialysis wherein decomposition of glucose contained therein is suppressed, and to methods for producing such solid preparations for dialysis.

BACKGROUND ART

In recent years, bicarbonate dialysates have come to be used more frequently in hemodialysis in favor of acetic acid-containing dialysates because bicarbonate dialysates impose less burden on a patient's body as compared to acetic acid-containing ones. However, it is difficult to prepare a one-pack type bicarbonate-containing preparation for dialysis due to the reactions between bicarbonate ions and magnesium or calcium ions contained therein as electrolytes for producing insoluble compounds (metal bicarbonate salts such as calcium bicarbonate and magnesium bicarbonate).

Therefore, a typical bicarbonate-containing preparation for dialysis consists of two components of a concentrate liquid agent "A" containing electrolytes such as calcium and magnesium ions, as well as glucose and a pH adjusting agent if necessary, and a powdery agent "B" containing sodium hydrogencarbonate of bicarbonate ions.

However, abovementioned concentrate liquid agent "A" is typically packed in a polyethylene bag in the amount between about 5 L and 15 L. The weight and transportation costs of the bag, storage space in hospital and disposal of waste fluid are a great burden.

As a solution to above problems, it has been suggested providing agent "A" in powder, and powdery agent "A" products are now commercially available (Patent literature 1). Such an agent "A" is typically a powdery or granular preparation made from a mixture of powdery ingredients, which are granulated, if necessary with a binder solution, subsequently dried and sieved.

In conventional powdery or granular preparations for dialysis, however, particles of ingredients are typically fine, and dust rises when the powders or granules are put into a dissolving machine. Additionally, conventional powdery or granular preparations for dialysis often have a strong smell caused by acetic acid contained therein as a pH adjusting agent. The above problems deteriorate working environment in production sites and healthcare sites.

In addition, acetic acid, which is contained slightly in conventional preparations for dialysis as a pH adjusting agent, practically does not exist in the living body by nature (0.1 mEq/L or less). Further, it has recently been recognized problematic that acetic acid may cause undesirable clinical symptoms such as headache or blood pressure reduction during a dialysis treatment.

In other words, it was considered not problematic to add a slight amount of acetic acid like between about 8 and 12 mEq/L in a bicarbonate-containing preparation for dialysis as a pH adjusting agent. However, prolongation of dialysis treatment and improvements in dialyzer's performance in recent years have resulted in excessively loading acetic acid contained in a dialysate on a patient's body and causing adverse effects on cardiovascular system. In parallel, adverse effects of acetic acid such as acetate intolerance have been recognized more severe than ever thought. To solve these problems, acetate-free preparations for dialysis containing solid organic acids such as citric acid have been developed (Patent literatures 2 and 3).

Solid organic acids such as citric acid contained in a preparation for dialysis as pH adjusting agents cause decomposition of glucose due to their strong acidic nature when stored for a long time under a condition that allows direct contact between solid organic acids and glucose. The decomposition of glucose produces decomposition products such as 5-hydroxymethyl furfural (5-HMF), and such decomposition of glucose increases under a condition of overhydration.

When acetic acid and acetate salts (sodium acetate) are used as conventional pH adjusting agents, acetic acid quickly permeates solid sodium acetate to adjust a pH ranging between 4 and 5. This prevents direct contact between acetic acid and glucose and, therefore, the decomposition of glucose is not a problem. However, the decomposition of glucose becomes a crucial problem when non-acetate solid organic acids are used as pH adjusting agents. Therefore, there is a need for development of a powdery or granular preparation for dialysis wherein the decomposition of glucose is suppressed.

[Patent literature 1] Japanese Patent Examined Publication No. Sho 57-88116
[Patent literature 2] Japanese Laid-open Patent Publication No. Hei 9-301875
[Patent literature 3] Japanese Laid-open Patent Publication No. 2005-330241

DISCLOSURE OF THE INVENTION

Problems to be Solved by the Invention

In view of the above circumstances, the present invention has as one object to provide a solid preparation for dialysis wherein glucose decomposition is suppressed, among powdery or granular preparations for dialysis containing acetate-free solid organic acids as pH adjusting agents.

To solve aforementioned problems, the present inventors have diligently researched and found that the problems will be solved by reducing the content of microparticles of solid organic acids, more specifically, by controlling the content percentage of solid organic acid particles whose diameters are less than a certain size, or by coating solid organic acids, and completed the present invention.

Means for Solving the Problems

A first basic embodiment of the present invention is a solid preparation for dialysis containing electrolytes, glucose and pH adjusting agents, comprises containing of solid organic acids whose 20 or less percent of particles are 150 μm or less in diameter.

More preferably, a second embodiment of the invention is a solid preparation for dialysis containing solid organic acids whose 10 or less percent of particles are 150 μm or less in diameter.

A third basic embodiment of the invention is a solid preparation for dialysis containing electrolytes, glucose and pH adjusting agents, characterized in that solid organic acids contained therein are coated.

More specifically, in each of abovementioned embodiments, the present invention relates to:

(1) an abovementioned solid preparation for dialysis characterized in that the solid organic acid contained therein is citric acid, and (2) an abovementioned solid preparation for dialysis characterized in that sodium citrate solution is used for coating solid organic acids contained therein.

Further, another embodiment of the invention is a method for producing a solid preparation for dialysis. More specifically, another embodiment of the invention is a method for producing a solid preparation for dialysis containing electrolytes, glucose and pH adjusting agents; the method characterized in that solid organic acids whose less than 10 percent of particles are 250 μm or less in diameter are added to dried granules composed of electrolytes and glucose. Another embodiment of the invention is a method for producing a solid preparation for dialysis containing electrolytes, glucose and pH adjusting agents; the method characterized in that solid organic acids coated with sodium citrate are added to dried granules composed of electrolytes. Yet specifically, another embodiment of the invention is the abovementioned methods for producing a solid preparation for dialysis characterized in that the solid organic acid contained therein is citric acid.

Furthermore, another basic embodiment of the invention is a solid preparation for dialysis containing electrolytes, glucose and pH adjusting agents characterized in that solid organic acids containing reduced amount of microparticles are used.

More preferably, another embodiment of the invention is an abovementioned solid preparation for dialysis characterized in that solid organic acids whose 20 or less percent of particles are 250 μm or less in diameter are used, and more specifically, characterized in that the solid organic acid is citric acid.

Yet another embodiment of the invention is a method for producing a solid preparation for dialysis containing electrolytes, glucose and pH adjusting agents; the method characterized in that solid organic acids containing reduced amount of microparticles are added to dried granules composed of electrolytes and glucose. Preferably, the method is characterized in that solid organic acids whose 20 or less percent of particles are 250 μm or less in diameter, or solid organic acids whose 10 or less percent of particles are 150 μm or less in diameter, are added.

Further, yet another embodiment of the invention is a method for producing a solid preparation for dialysis containing electrolytes, glucose and pH adjusting agents; the method characterized in that solid organic acids containing reduced amount of microparticles, the solid organic acids coated with glucose or sodium citrate, are added to dried granules composed of electrolytes.

Moreover, another embodiment of the invention is a preparation for dialysis in artificial kidney, comprising a combination between any of abovementioned solid preparations for dialysis of the invention and an agent B composed of sodium hydrogencarbonate.

Effects of the Invention

An advantage of a solid preparation for dialysis provided by the invention is to provide a stable powdery or granular preparation for dialysis causing no adverse effects such as acetate intolerance and allowing suppression of production of glucose decomposition products such as 5-hydroxymethyl furfural (5-HMF), owing to the use of acetate-free solid organic acids as pH adjusting agents.

BEST MODE FOR CARRYING OUT THE INVENTION

A solid preparation for dialysis provided by the invention is an agent "A" comprising electrolytes, pH adjusting agents and glucose. The agent "A" is diluted to a proper concentration and mixed with agent "B" comprising sodium hydrogencarbonate to be used as a perfusion fluid for hemodialysis. A preferred concentration of the fluid is as follows:

| | |
|---|---|
| $Na^+$ | 130-145 mEq/L |
| $K^+$ | 0-4 mEq/L |
| $Ca^{++}$ | 0-4 mEq/L |
| $Mg^{++}$ | 0-2 mEq/L |
| $Cl^-$ | 55-135 mEq/L |
| $HCO_3^-$ | 20-45 mEq/L |
| Solid organic acid ions | 0.02-10 mEq/L |
| Glucose | 0-2.0 g/L |

Most preferred electrolytes include sodium chloride, potassium chloride, calcium chloride and magnesium chloride. If necessary, other electrolytes can be used additionally without limitation.

Preferred solid organic acids serving as pH adjusting agents include citric acid, lactic acid, malic acid, ascorbic acid, succinic acid, maleic acid, malonic acid and fumaric acid, used solely or in combination. Most preferred solid organic acid serving as a pH adjusting agent is citric acid.

In a solid preparation for dialysis provided by the invention, it is preferable to use the above solid organic acids serving as pH adjusting agents, the solid organic acids containing reduced amount of particles pulverized into microparticles.

More specifically, it is preferable to use the solid organic acid having the content percentage of particles sized 250 μm or less in diameter is 20 percent or less, and more preferably 10 percent or less, or the content percentage of particles sized 150 μm or less in diameter is 10 percent or less, and more preferably 5 percent or less; as a means for inhibiting or minimizing direct contact between solid organic acids and glucose or chlorides of electrolytes such as sodium chloride and calcium chloride contained together.

In another embodiment, the solid organic acids serving as pH adjusting agents are coated. It is preferable to coat the surface of solid organic acids with glucose or sodium citrate, employing a glucose solution or a solution of sodium citrate serving as pH adjusting agent.

For the above coating, general coating methods such as fluidized bed granulation, agitating granulation and pan coating can be used.

A solid preparation for dialysis provided by the invention is a powdery or granular preparation containing electrolytes, glucose and the aforementioned special solid organic acids as pH adjusting agents. A method for producing the preparation comprises adding solid organic acids to dried granules composed of electrolytes and, if necessary, glucose.

Preferably, in the granulation process, general granulation methods and granulators used for granulating general solid preparations for dialysis are used. Yet preferably, but not limited to, a wet granulation method comprising kneading, granulating and drying, with a binder solution being added, is used. In the above process, it is preferable to use mixers capable of homogeneous kneading and granulating such as vertical granulators and high-speed mixers.

For granulation in the present invention, it is preferable to use calcium chloride and/or magnesium chloride dissolved into water and/or ethanol serving as a binder solution. The amount of water and/or ethanol for dissolution is preferably between about 0.2 and 20 percent, more preferably between about 0.3 and 10 percent and further more preferably between about 0.5 and 5 percent by weight of all ingredients. When the moisture percentage of the binder solution falls below 0.2 percent, particle binding and aggregating effects become so weak that granulation does not proceed efficiently. When the moisture percentage of the binder solution exceeds 20 percent, powders become so wet and sticky in a granulator that granulation becomes difficult.

By particle size distribution, preferably particles sized between 150 µm and 1700 µm are at least 95 percent, more preferably particles sized between 150 µm and 1400 µm are at least 95 percent, and further more preferably particles sized between 250 µm and 1200 µm are at least 95 percent; for the sake of homogeneity of mixture of granules and solid organic acids, as well as for the sake of preventing deterioration of environment (and erosion of devices) by powdery dust on use of the preparation.

The abovementioned "weight of all ingredients" means the gross weight of all ingredients used for granulation out of electrolytes and pH adjusting agents composing a preparation for dialysis.

Depending on the gross weight of all ingredients, the amount of water and/or ethanol may be small and easily saturated when calcium chloride and/or magnesium chloride are dissolved, leaving a part of calcium chloride and/or magnesium chloride undissolved. In such a case, either of calcium chloride or magnesium chloride, or a portion of calcium chloride and magnesium chloride, can be dissolved to be used as a binder. In such a case, preferably, the rest of calcium chloride and/or magnesium chloride that are not dissolved to make a binder solution are pulverized with other ingredients and granulated.

With respect to methods for adding a binder solution, methods that are capable of adding the binder solution uniformly without production of rough particles to produce a preparation excellent in content homogeneity are used. It is preferable, for example, to spray or drop a binder solution onto powders while the powders are being mixed. As abovementioned, use of calcium chloride and/or magnesium chloride, which are deliquescent, as a binder solution enables production of a solid preparation for dialysis excellent in content homogeneity.

In addition, by using water and/or ethanol in the amount between about 0.2 and 20 percent by weight of all ingredients for dissolution, water and/or ethanol content can be curbed low, and, therefore, drying time can be shortened. As a result, a preparation that is also excellent in production efficiency and does not easily decompose can be produced.

In an embodiment of the invention, a process of crushing each ingredient into particles sized about 1.5 mm or less can be added in order to uniform particle size before granulation. This process enables homogeneous mixing of ingredients in the subsequent granulation process and, consequently, enables production of a preparation for dialysis excellent in homogeneity. In the above crushing process, it is preferable to crush electrolytes composing a preparation for dialysis, except for calcium chloride and/or magnesium chloride that are used as a binder, into particles sized about 1.5 mm or less. For crushing, a general sieving mill can be used if it is capable of crushing each ingredient into the size of 1.5 mm or less. Preferably, average size of crushed particles is between 12 and 100 standard sieve mesh.

In the abovementioned crushing process, in another embodiment, sodium chloride can be separately crushed into the size of about 1.5 mm or less. In other words, electrolytes except for sodium chloride can be granulated, sieved and dried to produce sodium chloride-free granules to be used for a preparation for dialysis; and then crushed sodium chloride can be mixed to the above granules or separately packed to produce a preparation for dialysis.

Because sodium chloride composes between about 60 and 80 percent by weight of all ingredients of a solid preparation for dialysis provided by the invention, it is an advantage of producing sodium chloride-free granules that manufacturing devices can be downscaled for reduction of production costs and improvement of production efficiency.

Furthermore, in an embodiment, crushed sodium chloride and sodium chloride-free granules can be packed separately in a multi-chamber container having compartments. This allows the compartments to be opened simultaneously for prevention of missing or incorrectly mixing ingredients and, therefore, allows an easy-handling preparation for dialysis to be provided.

With respect to drying devices for drying granules that are granulated and sieved as aforementioned, general dryers used for granulation and drying processes of solid preparations for dialysis including, for example, fluidized-bed dryers and vibrating dryers, can be used.

Subsequently, pH adjusting agents of solid organic acids unique to the present invention are added to the abovementioned dried granules. It is an advantage of the invention that production of glucose decomposition products such as 5-HMF is effectively suppressed by adding solid organic acids to previously-dried granules composed of electrolytes and other ingredients to provide a stable solid preparation for dialysis.

In the above adding process, general mixers can be used without limitation.

In the present invention, it is preferable to granulate glucose with electrolytes previously, when glucose is not used for coating solid organic acids. In another embodiment, glucose can be added at the same time when the solid organic acids serving as pH adjusting agents are added to dried granules composed of electrolytes.

In another embodiment, it is preferable to add glucose to dried granules composed of electrolytes prior to adding solid organic acids.

A solid preparation for dialysis of the present invention prepared according to the aforementioned processes is packed in a suitable container and provided as an agent "A" for dialysis. It is preferable to use a container capable of preventing transmission of water vapor and gases, for example, such as having water vapor transmission rates of 1.0 g/m²/24 hrs or less (under 40° C., 90% RH). Preferred materials for the container include laminated packing materials such as PET, glass-vapor deposited PET, PE; PET, aluminum oxide, nylon; PET, SiOx, CPP; PET, SiOx, nylon, CPP; and OPP, SiOx, CPP.

EXAMPLES

By way of test and working examples, and not limitation, detailed description of the invention will be set forth.

Test Example 1

Among Solid Citric Acid Serving as a pH Adjusting Agent, Effects of Existence of Citric Acid Whose Particles are 150 µm or Less in Diameter on Glucose Decomposition Solid preparations for dialysis prepared according to the prescription in Table 1 were used. The solid preparations for dialysis were obtained by the following methods; as a pH adjusting agent, citric acid of solid organic acid passing a 100-mesh sieve (150 μm or less) were added by different adding ratios to dried granules composed of sodium chloride, potassium chloride, calcium chloride, magnesium chloride, glucose and sodium chloride.

TABLE 1

| | |
|---|---|
| Sodium chloride | 2148 g |
| Potassium chloride | 52 g |
| Calcium chloride | 77 g |
| Magnesium chloride | 36 g |
| Glucose | 525 g |
| Sodium citrate | 10 g |
| Citric acid | 35 g |

The mixtures were stored at the temperature of 50° C. On the third, fifth and tenth days of storage, the production of 5-hydroxymethyl furfural (5-HMF) which is glucose decomposition product, was measured.

The amount of produced 5-HMF was quantified by dissolving a 2.9 g of sample into 21 mL of water and measuring absorbance at 284 nm with a spectrophotometer.

The results are shown in FIG. 1.

As is apparent from FIG. 1, the more citric acid passing a 100-mesh sieve (150 μm or less) was added, the more production of glucose decomposition product 5-HMF increased. When the adding ratio of citric acid passing a 100-mesh sieve (150 μm or less) was 20 percent or less, 5-HMF production suppressing effect was observed. When the adding ratio was 10 percent or less, 5-HMF production was suppressed markedly.

Test Example 2

Effects of Existence of Citric Acid Pulverized into Microparticles (250 μm or Less in Diameter, and 150 μm or Less in Diameter) on Glucose Decomposition As detailed in Table 2 below, 4.9 g of citric acid containing citric acid pulverized into microparticles passing a 60-mesh sieve (250 μm or less) and a 100-mesh sieve (150 μm or less) was used. The citric acid was mixed with 400 g of dried granules obtained in Working Example 1 below. The mixtures were stored at the temperature of 60° C. for 20 hours. Then, the production of 5-hydroxymethyl furfural (5-HMF) which is glucose decomposition product, was measured.

The amount of produced 5-HMF was quantified by dissolving the samples to the glucose concentration of 2.5% and measuring absorbance at 284 nm with a spectrophotometer.

The results are shown in Table 2, also.

TABLE 2

| Content of Microparticles in Citric Acid Added to Dried Granules (%) | | |
|---|---|---|
| Particle size: 150 μm or less (Passing a 100-mesh sieve) | Particle size: 250 μm or less (Passing a 60-mesh sieve) | 5-HMF Absorbance (60° C./20 hrs.) |
| 0.01 | 0.01 | 0.033 |
| 0.00 | 0.00 | 0.022 |
| 0.05 | 0.05 | 0.029 |
| 2.21 | 4.22 | 0.070 |
| 5.51 | 10.31 | 0.129 |
| 8.02 | 15.33 | 0.169 |
| 19.87 | 33.03 | 0.233 |
| 26.72 | 44.56 | 0.336 |
| 56.90 | 81.08 | 0.505 |

Based on the results shown in Table 2 above, the results depending upon the content of citric acid microparticles passing a 100-mesh sieve (150 μm or less) in citric acid are shown in FIG. 2.

Further, based on the above results, the results depending upon the content of citric acid microparticles passing a 60-mesh sieve (250 μm or less) in citric acid are shown in FIG. 3.

The results shown in Table 2, FIG. 2 and FIG. 3 demonstrate that the more citric acid microparticles are contained in the citric acid added to dried granules, the more production of glucose decomposition product 5-HMF increases; that the fewer citric acid microparticles passing a 100-mesh sieve (150 μm or less) are contained, the more 5-HMF production-suppressing effects are observed; and that, when the content of citric acid microparticles passing a 100-mesh sieve (150 μm or less) is less than 10%, 5-HMF production is suppressed markedly.

With respect to the content of citric acid particles passing a 60-mesh sieve (250 μm or less), it is demonstrated that 5-HMF production is suppressed markedly when the content is 20% or less, and preferably, when the content is 10% or less.

Test Example 3

Whether Microparticles Existing in Dried Granules Prior to Mixing Citric Acid Affect Glucose Decomposition or Not Samples A, B and C of dried granules obtained in Working Example 1 below, the samples containing different amount of microparticles (passing a 100-mesh sieve [150 μm or less]) respectively, were stored at the temperature of 60° C. for 20 hours. Then, the production of 5-hydroxymethyl furfural (5-HMF) which is glucose decomposition product, was measured.

The content of microparticles (passing a 100-mesh sieve [150 μm or less]) in the samples A, B and C are shown in Table 3 below.

TABLE 3

| Content of Particles Sized | 5-HMF Absorbance (60° C./20 hrs.) | | |
|---|---|---|---|
| 150 μm or Less (%) (Passing a 100-mesh Sieve) | Sample A (5 samples) | Sample B (3 samples) | Sample C (2 samples) |
| 0.0 | 0.024 | 0.023 | |
| 2.45 | 0.021 | | |
| 2.59 | | | 0.021 |
| 2.89 | 0.26 | | |
| 3.80 | | 0.025 | |
| 4.65 | | | 0.022 |
| 4.74 | | 0.027 | |
| 5.11 | 0.033 | | |
| 8.96 | 0.035 | | |

The amount of produced 5-HMF was quantified by dissolving the samples to the glucose concentration of 2.5% and measuring absorbance at 284 nm with a spectrophotometer.

The results are shown in Table 3, also.

Based on the results shown in Table 3 above, the 5-HMF absorbance of each sample containing dried granules pulverized into microparticles passing a 100-mesh sieve (150 μm or less) is shown in FIG. 4.

As is apparent from the results shown in FIG. 4, when dried granules contain microparticles of the same dried granules, existence of the microparticles practically does not affect glucose decomposition.

The results of Test Examples 1, 2 and 3 demonstrate characteristics of the present invention that reduction of additive amount of citric acid pulverized into microparticles, in other words, use of solid organic acids such as citric acid containing reduced amount of particles pulverized into microparticles, provides a stable solid preparation for dialysis wherein glucose decomposition is suppressed, among solid preparations for dialysis containing electrolytes, glucose and pH adjusting agents.

Working Example 1

Formulation of a Solid Preparation for Dialysis

In a vertical granulator (VG-25 by Powlex Co., Ltd.), 9429 g of sodium chloride, 228 g of potassium chloride, 338 g of calcium chloride, 42 g of sodium citrate and 2305 g of glucose were mixed. The mixture was kneaded and mixed while a binder solution made from 158 g of magnesium chloride dissolved into 11 L of water (1 percent) was being added. Then, the obtained granules were dried in a fluidized bed dryer.

Subsequently, to 2848 g of above dried granules, 34 g of citric acid whose less than 5 percent of particles were 150 μm or less in diameter was added in a V-type mixer to obtain a solid preparation for dialysis of the invention.

Industrial Applicability

As aforementioned, the present invention has a great medical value from the viewpoint that the present invention provides a powdery or granular stable preparation for dialysis wherein glucose decomposition is suppressed, among solid preparations for dialysis containing electrolytes, glucose and pH adjusting agents.

Figure 1:
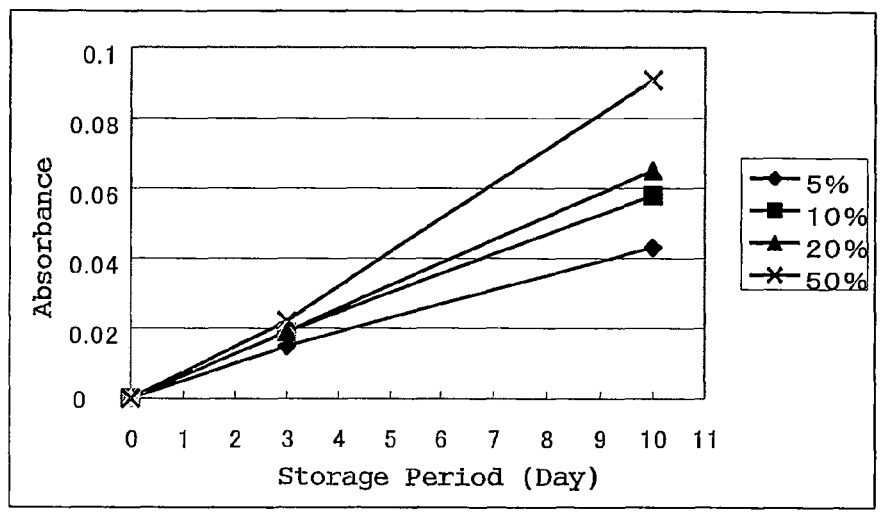
FIG. 1 shows the production amount of 5-hydroxymethyl furfural (5-HMF) in different adding ratios of citric acid passing a 100-mesh sieve (150 μm or less) in Test Example 1.
Figure 2:
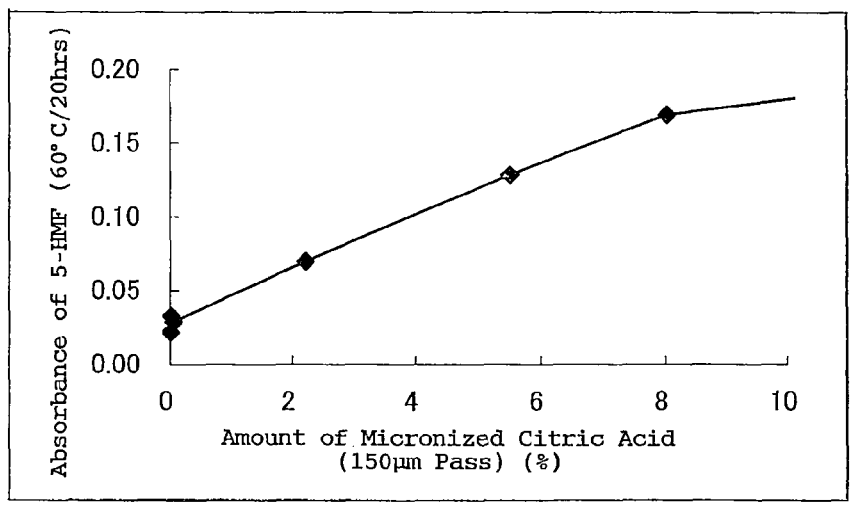
FIG. 2 shows the production amount of 5-hydroxymethyl furfural (5-HMF) in different content percentages of citric acid passing a 100-mesh sieve (150 μm or less) in Test Example 2.
Figure 3:
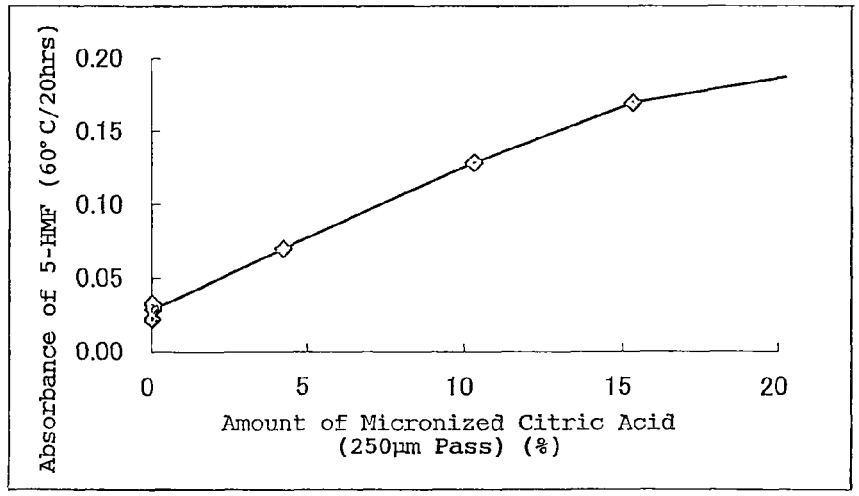
FIG. 3 shows the production amount of 5-hydroxymethyl furfural (5-HMF) in different content percentages of citric acid passing a 60-mesh sieve (250 μm or less) in Test Example 2.
Figure 4:
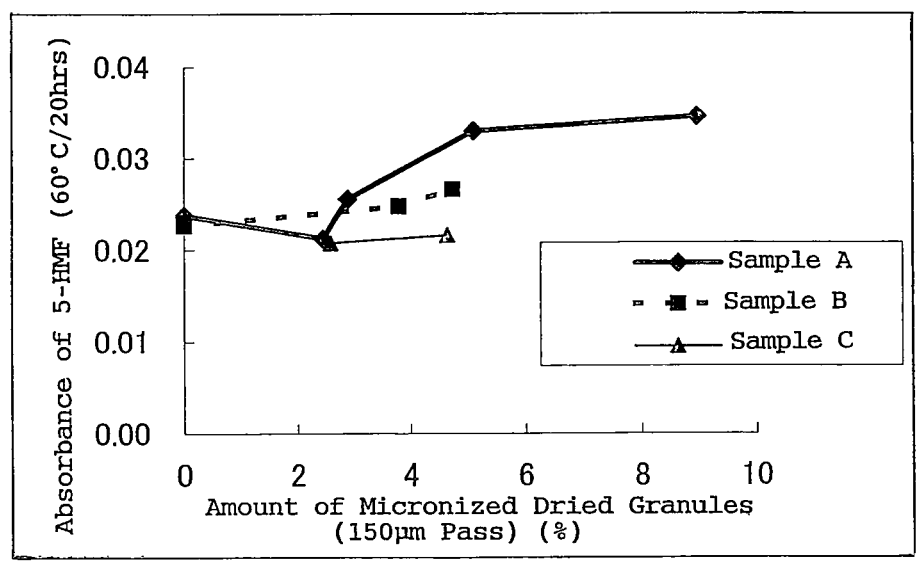
FIG. 4 shows the production amount of 5-hydroxymethyl furfural (5-HMF) depending upon content percentages of microparticles of dried granules prior to mixing citric acid in Test Example 3.

The invention claimed is:

1. A solid preparation for dialysis in which production of 5-hydroxymethyl furfural (5-HMF) from glucose contained therein is suppressed, comprising:
   (a) particles of solid citric acid as a pH adjusting agent, wherein said particles of solid citric acid optionally comprise one or more additional organic acid,
   (b) electrolytes, and
   (c) glucose,
wherein
   20% or less of said particles of solid citric acid have a particle diameter of 150 μm or less,
   said solid preparation is prepared by adding said particles of solid citric acid to a dry granulated composition comprising the electrolytes and glucose, and
   said solid preparation is acetate free.

2. The solid preparation for dialysis of claim 1, wherein 10 or less percent of said particles of solid citric acid have a particle diameter of 150 μm or less.

3. The solid preparation for dialysis of claim 1, wherein said particles of solid citric acid comprise said one or more additional organic acid.

4. The solid preparation for dialysis of claim 3, wherein said additional organic acid is selected from the group consisting of lactic acid, malic acid, ascorbic acid, succinic acid, maleic acid, malonic acid and fumaric acid.

5. The solid preparation for dialysis of claim 1, which consists essentially of the particles of solid citric acid, electrolytes and glucose.

6. The solid preparation for dialysis of claim 1, which consists of the particles of solid citric acid, electrolytes and glucose.

7. A preparation for dialysis in an artificial kidney, comprising:
   (A) the solid preparation for dialysis of claim 1, and
   (B) sodium hydrogencarbonate.

8. A preparation for dialysis in an artificial kidney, comprising:
   (A) the solid preparation for dialysis of claim 2, and
   (B) sodium hydrogencarbonate.

9. A preparation for dialysis in an artificial kidney, comprising:
   (A) the solid preparation for dialysis of claim 3, and
   (B) sodium hydrogencarbonate.

10. A preparation for dialysis in an artificial kidney, comprising:
    (A) the solid preparation for dialysis of claim 4, and
    (B) sodium hydrogencarbonate.

11. A preparation for dialysis in an artificial kidney, comprising:
    (A) the solid preparation for dialysis of claim 5, and
    (B) sodium hydrogencarbonate.

12. A preparation for dialysis in an artificial kidney, comprising:
    (A) the solid preparation for dialysis of claim 6, and
    (B) sodium hydrogencarbonate.

* * * * *